United States Patent [19]
Zocchi et al.

[11] Patent Number: 6,087,402
[45] Date of Patent: *Jul. 11, 2000

[54] FOAM CLEANING COMPOSITIONS

[75] Inventors: Germaine Zocchi, Villers-Aux-Tours; Pierre Fonsny, Fays, both of Belgium

[73] Assignee: Colgate Palmolive Company, New York, N.Y.

[ * ] Notice: This patent is subject to a terminal disclaimer.

[21] Appl. No.: 08/938,684

[22] Filed: Sep. 26, 1997

Related U.S. Application Data

[63] Continuation-in-part of application No. 08/753,161, Nov. 21, 1996, Pat. No. 5,906,992.

[51] Int. Cl.$^7$ .......................... A01N 25/16; A01N 35/04; A01N 43/30; A01N 65/00; A01N 25/30; C11D 3/48

[52] U.S. Cl. ........................ 514/699; 514/464; 514/531; 514/544; 514/678; 514/686; 514/688; 514/690; 514/692; 514/693; 514/698; 514/723; 514/729; 514/730; 514/739; 514/763; 514/875; 514/945; 424/195.1; 424/196.1; 424/126; 424/405; 424/43; 510/382; 510/383; 510/386; 510/401

[58] Field of Search ...................... 514/544, 699, 514/686, 688, 723, 690, 692, 763, 730, 693, 698, 678, 739, 729, 531, 464, 875, 945; 424/196.1, 195.1, 126, 405, 43; 510/382, 383, 386, 401

[56] References Cited

U.S. PATENT DOCUMENTS

| | | | |
|---|---|---|---|
| 4,666,940 | 5/1987 | Bischoff et al. | 514/544 |
| 5,906,992 | 5/1999 | Fonsny et al. | 514/464 |

FOREIGN PATENT DOCUMENTS 8912673  12/1989  WIPO .

*Primary Examiner*—John Pak
*Attorney, Agent, or Firm*—Richard E. Nanfeldt

[57] ABSTRACT

The present invention relates to a foam composition for killing dust mites comprising an acaricidal agent, polymer, ether solvent, perfume, surfactant and water.

5 Claims, No Drawings

FOAM CLEANING COMPOSITIONS

RELATED APPLICATION

This application is a continuation in part application of U.S. Ser. No. 08/753,161 filed Nov. 21, 1996 now U.S. Pat. No. 5,906,922.

FIELD OF THE INVENTION

This invention relates to a foam compositions which are used for treating textile surfaces of interior furnishings such as carpets, mattresses and chairs for the purpose of killing dust mites.

BACKGROUND OF THE INVENTION

A major problem existing in households is the presence of house dust mites which release allergens. Dust mites flourish in textile materials such as carpets, upholstered chairs and mattresses.

U.S. Pat. No. 4,666,940 teaches a textile cleaning composition containing benzyl benzoate as an acaricidal agent, a surfactant and a polymeric material.

European Patent No. 17,315 has disclosed that normal insecticides, such as pyrethrins or DDT, are relatively ineffective against house dust mites. According to this patent specification, benzyl benzoate is regarded as a suitable active substance, and the aim of that patent is to diminish a disadvantage of this compound, namely the relatively high vapor pressure, in order to achieve longer retention of the substance. For this purpose, combinations of benzyl benzoate with fatty acid esters and a fungicidal agent in a nonaqueous preparation are proposed therein.

According to British Patent No. 1,368,657, teaches the adding of nonvolatile polyalkylene glycols or nonvolatile ethers or esters to benzyl benzoate. However, this has caused considerable disadvantages in the use of the beds, and these are documented in detail in European Patent No. 17,315. In both literature references, the carrier substances used are volatile organic solvents.

SUMMARY OF THE INVENTION

The present invention relates to a foam composition which is effective in killing dust mites. The foam cleaning composition contains a polyacrylate polymer, a hydrocarbon propellant, an ether type solvent, an acaricidal agent a surfactant, a hydrotrope, perfume, an anticorrision agent and water, wherein the composition does not contain benzyl benzoate.

An object of the instant composition is to provide a foam composition which is effective in killing dust mites and that the treating foam composition be readily removed from the treated surface by post vacuuming.

DETAILED DESCRIPTION OF THE INVENTION

The present invention relates to a foam composition for killing dust mites which comprises approximately by weight:

(a) 0.5% to 10%, more preferably 1% to 8% of a polyacrylate polymer having a molecular weight of about 100,000 to about 900,000;

(b) 2% to 10%, more preferably 3% to 8% of a hydrocarbon propellant which can be a mixture of isobutane and propane;

(c) 0.5% to 5%, more preferably 0.75% to 3% of pentasodium triphosphate;

(d) 0.5% to 3%, more preferably 0.75% to 2% of an ether solvent;

(e) 0.1% to 5%, more preferably 0.5% to 4% of an acaricidal agent;

(f) 0.1% to 5%, more preferably 0.25% to 2% of at least one surfactant;

(g) 0.1% to 3%, more preferably 0.25% to 2% of a hydrotrope;

(h) 0.1% to 1%, more preferably 0.2% to 0.8% of a perfume;

(i) 0.01% to 5%, more preferably 0.02% to 3% of an anticorrosion agent; and (j) the balance being water, wherein the foam composition does not contain benzyl benzoate.

The polyacrylate polymer useful in the instant invention has a molecular weight of about 100,000 to about 900,000, more preferably about 400,000 to about 700,000. A preferred polymer is Ubatol VTR455 which is manufactured by Cray Valley and is an aqueous emulsion of a polyacrylate polymer which contains 24 wt. % of polyacrylate polymer, 10 wt. % of a paraffin sulfonate surfactant and the balance being water.

The propellant gas mixture can be any conventionally employed propellant gas but a preferred mixture is isobutane and propane in a weight ratio of about 6:1 to 1:1.

The ether solvents used in the instant compositions are glycol ethers such as ethylene glycol monobutyl ether (butyl cellosolve), diethylene glycol monobutyl ether (butyl carbitol), triethylene glycol monobutyl ether, mono, di, tri propylene glycol monobutyl ether, tetraethylene glycol monobutyl ether, mono, di, tripropylene glycol monomethyl ether, propylene glycol monomethyl ether, ethylene glycol monohexyl ether, diethylene glycol monohexyl ether, propylene glycol tertiary butyl ether, ethylene glycol monoethyl ether, ethylene glycol monomethyl ether, ethylene glycol monopropyl ether, ethylene glycol monopentyl ether, diethylene glycol monomethyl ether, diethylene glycol monoethyl ether, diethylene glycol monopropyl ether, diethylene glycol monopentyl ether, triethylene glycol monomethyl ether, triethylene glycol monoethyl ether, triethylene glycol monopropyl ether, triethylene glycol monopentyl ether, triethylene glycol monohexyl ether, mono, di, tripropylene glycol monoethyl ether, mono, di tripropylene glycol monopropyl ether, mono, di, tripropylene glycol monopentyl ether, mono, di, tripropylene glycol monohexyl ether, mono, di, tributylene glycol mono methyl ether, mono, di, tributylene glycol monoethyl ether, mono, di, tributylene glycol monopropyl ether, mono, di, tributylene glycol monobutyl ether, mono, di, tributylene glycol monopentyl ether and mono, di, tributylene glycol monohexyl ether, ethylene glycol monoacetate and dipropylene glycol propionate.

The anionic sulfonate surfactants which may be used in the compositions of this invention are water soluble and include the sodium, potassium, ammonium and ethanolammonium salts of linear $C_8$–$C_{16}$ alkyl benzene sulfonates; $C_{10}$–$C_{20}$ paraffin sulfonates, alpha olefin sulfonates containing about 10–24 carbon atoms and $C_8$–$C_{18}$ alkyl sulfates and mixtures thereof. The preferred anionic sulfonate surfactants are a paraffin sulfonate or alkyl benzene sulfonate.

The paraffin sulfonates may be monosulfonates or di-sulfonates and usually are mixtures thereof, obtained by sulfonating paraffins of 10 to 20 carbon atoms. Preferred paraffin sulfonates are those of $C_{12-18}$ carbon atoms chains, and more preferably they are of $C_{14-17}$ chains. Paraffin sulfonates that have the sulfonate group(s) distributed along the paraffin chain are described in U.S. Pat. Nos. 2,503,280; 2,507,088; 3,260,744; and 3,372,188; and also in German Patent 735,096. Such compounds may be made to specifications and desirably the content of paraffin sulfonates outside the $C_{14-17}$ range will be minor and will be minimized, as will be any contents of di- or poly-sulfonates.

Examples of suitable other sulfonated anionic detergents are the well known higher alkyl mononuclear aromatic sulfonates, such as the higher alkylbenzene sulfonates containing 9 to 18 or preferably 9 to 16 carbon atoms in the higher alkyl group in a straight or branched chain, or $C_{8-15}$ alkyl toluene sulfonates. A preferred alkylbenzene sulfonate is a linear alkylbenzene sulfonate having a higher content of 3-phenyl (or higher) isomers and a correspondingly lower content (well below 50%) of 2-phenyl (or lower) isomers, such as those sulfonates wherein the benzene ring is attached mostly at the 3 or higher (for example 4, 5, 6 or 7) position of the alkyl group and the content of the isomers in which the benzene ring is attached in the 2 or 1 position is correspondingly low. Preferred materials are set forth in U.S. Pat. No. 3,320,174, especially those in which the alkyls are of 10 to 13 carbon atoms.

The $C_{8-18}$ ethoxylated alkyl ether sulfate surfactants have the structure

R——(OCHCH$_2$)$_n$OSO$_3^-$M$^+$ wherein n is about 1 to about 22 more preferably 1 to 3 and R is an alkyl group having about 8 to about 18 carbon atoms, more preferably 12 to 15 and natural cuts, for example, $C_{12-14}$ or $C_{12-16}$ and M is an ammonium cation or a metal cation, most preferably sodium. The ethoxylated alkyl ether sulfate is present in the composition at a concentration of about 8 to about 20 wt. %, more preferably about 10 to 18 wt. %.

The ethoxylated alkyl ether sulfate may be made by sulfating the condensation product of ethylene oxide and $C_{8-10}$ alkanol, and neutralizing the resultant product. The ethoxylated alkyl ether sulfates differ from one another in the number of carbon atoms in the alcohols and in the number of moles of ethylene oxide reacted with one mole of such alcohol. Preferred ethoxylated alkyl ether polyethenoxy sulfates contain 12 to 15 carbon atoms in the alcohols and in the alkyl groups thereof.

Ethoxylated $C_{8-18}$ alkylphenyl ether sulfates containing from 1 to 6 moles of ethylene oxide in the molecule are also suitable for use in the invention compositions. These detergents can be prepared by reacting an alkyl phenol with 1 to 6 moles of ethylene oxide and sulfating and neutralizing the resultant ethoxylated alkylphenol. The concentration of the ethoxylated alkyl ether sulfate surfactant is about 8 to about 20 wt. %. Other surfactants which can be used are disodium cocfatty ethanol amido sulfosuccinates and sarcosinates.

The instant composition can also contain a zwitterionic surfactant and/or an amine oxide surfactant at a concentration of 0 to 5 wt. %, more preferably 0.5 to 2.0 wt. %.

The zwitterionic surfactants are water soluble betaine having the general formula:

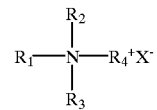

wherein $X^-$ is selected from the group consisting of $SO_3^-$ and $CO_2^-$ and $R_1$ is an alkyl group having 10 to about 20 carbon atoms, preferably 12 to 16 carbon atoms, or the amido radical:

wherein $R_5$ is an alkyl group having about 9 to 19 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N, N-dimethyl-ammonia) acetate, coco dimethyl betaine or 2-(N-coco N, N-dimethylammonia) acetate, myristyl dimethyl betaine, palmityl dimethyl betaine, lauryl dimethyl betaine, cetyl dimethyl betaine, stearyl dimethyl betaine, etc. The amidobetaines similarly include cocoamidoethylbetaine, cocoamidopropyl betaine and the like. Preferred betaines are coco ($C_8$–$C_{18}$) amidopropyl dimethyl betaine and lauryl dimethyl betaine.

The amine oxides are semi-polar nonionic surfactants which comprise compounds and mixtures of compounds having the formula:

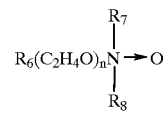

wherein $R_6$ is an alkyl, 2-hydroxyalkyl, 3-hydroxyalkyl, or 3-alkoxy-2-hydroxypropyl radical in which the alkyl and alkoxy, respectively, contain from 8 to 18 carbon atoms, $R_7$ and $R_8$ are each methyl, ethyl, propyl, isopropyl, 2-hydroxyethyl, 2-hydroxypropyl, or 3-hydroxypropyl, and n is from 0 to 10. Particularly preferred are amine oxides of the formula:

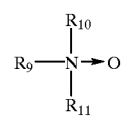

wherein $R_9$ is a $C_{12-16}$ alkyl group or amido radical:

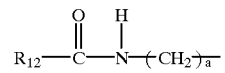

wherein $R_{12}$ is an alkyl group having about 9 to 19 carbon atoms and a is an integer 1 to 4 and $R_{10}$ and $R_{11}$ are methyl or ethyl. The above ethylene oxide condensates, amides, and amine oxides are more fully described in U.S. Pat. No. 4,316,824 which is hereby incorporated herein by reference.

Nonionic surfactants or lauryl myristyl monoethanolamide can be used at a concentration of 0 to 5 wt. %, more preferably 0.5 to 2 wt. % in the instant compositions.

The hydrotropes useful in the instant invention are sodium xylene sulfonate or sodium cumene sulfonate.

The acaricidal agents which are useful in the instant invention are selected from the group consisting of benzaldehyde, benzophenone, methyl salicylate, citral lemarome, acetophenone, citral dimethyl acetal, benzyl acetate, benzyl propionate, phenyl ethyl acetate, phenyl ethyl benzoate, carvone, aubepine, litsea oil, geranyl acetate, benzyl isoeugenone, isobutyl benzoate, terpinolene, rosemary oil, amyl salicylate, phenyl ethyl alcohol, eucalyptus globulus, decyl aldehyde, benzyl acetone, linalool, terpineol, citronella, D-phenothrin and piperonyl butoxide and mixtures thereof.

The anticorrision agents are selected from the group consisting of sodium nitrate, sodium silicate, sodium sarcosinate, sodium sulfosuccinate, sodium phosphate and sodium borate.

The following examples illustrate foam cleaning compositions of the described invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

The following compositions in wt. % were prepared at 25° C. by simple mixing:

|  | A | B | C | D | E | F | G |
|---|---|---|---|---|---|---|---|
| Polyacrylate polymer Ubatol VTR 455 | 3.84 | 3.84 | 3.84 | 3.84 | 3.84 | 3.84 | 3.84 |
| Sodium $C_{13}$–$C_{17}$ paraffin sulfonate | 1.6 | 1.6 | 1.6 | 1.6 | 1.6 | 1.6 | 1.6 |
| Pentasodium triphosphate | 2.2 | 2.2 | 2.2 | 2.2 | 2.2 | 2.2 | 2.2 |
| Perfume | 0.3 | 0.3 | 0.3 | 0.3 | 0.3 | 0.3 | 0.3 |
| Sodium silicate | 0.2 | 0.2 | 0.2 | 0.2 | 0.2 | 0.2 | 0.2 |
| Lauryl myristyl monoethanol amide | 0.5 | 0.5 | 0.5 | 0.5 | 0.5 | 0.5 | 0.5 |
| Sodium xylene sulfonate | 0.3 | 0.3 | 0.3 | 0.3 | 0.3 | 0.3 | 0.3 |
| Water | bal | bal | bal | bal | bal | bal | bal |
| Diethylene glycol monobutyl ether | 1 | 1 | 1 | 2 | 1 | 1 | 0 |
| Phenothrin |  |  |  | 0.15 |  |  |  |
| Piperonyl butoxide |  |  |  | 0.75 |  |  |  |
| Benzyl alcohol |  | 2 | 1 |  |  |  |  |
| Benzyl salicylate | 1 |  |  |  | 0.5 |  |  |
| Isobutane | 4.63 | 4.63 | 4.63 | 4.63 | 4.63 | 4.63 | 4.63 |
| Propane | 0.87 | 0.87 | 0.87 | 0.87 | 0.87 | 0.87 | 0.87 |
| Acaricidal tests: % dead dust mites |  |  |  |  |  |  |  |
| 30 min contact time - neat product | 100 | 100 | 100 | 100 | 0 | 0 | 0 |
| 3 h after carpet treatment | 89.9 | 49 | 34 | 81 |  |  |  |
| 24 h after carpet treatment | 91 | 55 | 22 | 99 |  |  |  |
| 96 h after carpet treatment | 92 | 98 | 65 | 100 |  |  |  |

The acaricidal test for mites is done, first, in liquid medium in 24 wells plastic plates. About 30 living mites are placed in the well with the nourishing culture medium and then covered with either water (background values) or the neat foam for carpet (or any other liquid product to be tested) in water and left in contact for 30 minutes. The remaining living mites are counted by observation under the microscope after the envisaged contact time. Contact times with mites can be 5 minutes up to 3 hours. When the foam for carpet has been found an acaricidal activity, the test is repeated on carpet pieces. Carpet pieces are infested with a known amount (80–100) of dust mites and let to settle for 1 hour. Carpet pieces are then treated with the acaricidal foam and the remaining living mites are counted by visual observation after 3 hours, 24 hours and 96 hours. The examination can be extended up to 7 days after the treatment.

What is claimed is:

1. A foam composition comprising approximately by weight:
   (a) 0.5% to 10% of a polyacrylate polymer;
   (b) 2% to 10% of a hydrocarbon propellant;
   (c) 0.5% to 5% of pentasodium triphosphate;
   (d) 0.5% to 3% of an ether solvent;
   (e) 0.1% to 5% of at least one acaricidal agent, wherein the acaricidal agent is selected from the group consisting of benzaldehyde, benzophenone, acetophenone, citral dimethyl acetal, carvone, litsea cubeba oil, terpinolene, rosemary oil, phenyl ethyl alcohol, eucalyptus globulus, decyl aldehyde, benzylacetone, linalool, terpineol, citronella, D-phenothrin and piperonyl butoxide and mixtures thereof;
   (f) 0.1% to 5% of a surfactant;
   (g) 0.1% to 3% of a hydrotrope;
   (h) 0.1% to 1% of a perfume;
   (i) 0.01% to 5% of an anticorrosion agent selected from the group consisting of sodium nitrate, sodium silicate, sodium sarcosinate, sodium sulfosuccinate and sodium borate; and
   (j) the balance being water, wherein the composition does not contain benzyl benzoate.

2. The composition according to claim 1 wherein said surfactant is an anionic surfactant.

3. The composition according to claim 2 further including a zwitterionic surfactant.

4. The composition according to claim 2 further including a nonionic surfactant.

5. The composition according to claim 1, wherein said hydrocarbon propellant is a mixture of propane and isobutane.

* * * * *